United States Patent [19]

Ureche et al.

[11] Patent Number: 5,106,367
[45] Date of Patent: Apr. 21, 1992

[54] EYE SURGERY APPARATUS WITH VACUUM SURGE SUPPRESSOR

[75] Inventors: Alexander Ureche, 27181 Valleymont, El Toro, Calif. 92630; Stephan Gaspar, Santa Ana, Calif.

[73] Assignee: Alexander Ureche, Mission Viejo, Calif.

[21] Appl. No.: 442,306

[22] Filed: Nov. 28, 1989

[51] Int. Cl.$^5$ .................................... A61M 1/00
[52] U.S. Cl. ....................... 604/30; 604/119; 604/247; 417/540
[58] Field of Search ............ 604/20, 22, 30, 31, 604/35, 118, 119, 246, 247, 129, 320, 323; 417/540

[56] References Cited

U.S. PATENT DOCUMENTS

| | | | |
|---|---|---|---|
| 1,579,891 | 4/1926 | Sandoz | 417/540 |
| 2,448,118 | 8/1948 | Pellettere | 417/540 |
| 3,469,582 | 9/1969 | Jackson | 604/119 |
| 3,851,661 | 12/1974 | Fernandez | 417/540 X |
| 3,874,417 | 4/1975 | Clay | 417/540 X |
| 4,041,947 | 8/1977 | Weiss et al. | 604/118 X |
| 4,062,360 | 12/1977 | Bentley | 604/119 |
| 4,921,477 | 5/1990 | Davis | 604/22 |

*Primary Examiner*—John D. Yasko
*Assistant Examiner*—Adam J. Cermak
*Attorney, Agent, or Firm*—Blakely, Sokoloff, Taylor & Zafman

[57] ABSTRACT

Collapse of the cornea into the cavity formed when material such as the lens is removed from an eye in the irrigation-aspiration method is minimized by incorporating a pressure responsive, variable flow resistance element in the aspiration line of the irrigation-aspiration apparatus. A preferred pressure responsive, variable resistance element is a length of thin walled tubing which is easily collapsed to smaller flow path area in response to increasing negative pressure in the aspiration line.

6 Claims, 1 Drawing Sheet

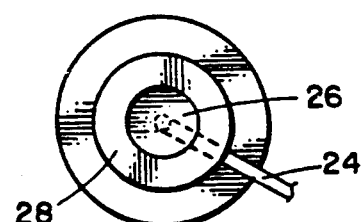
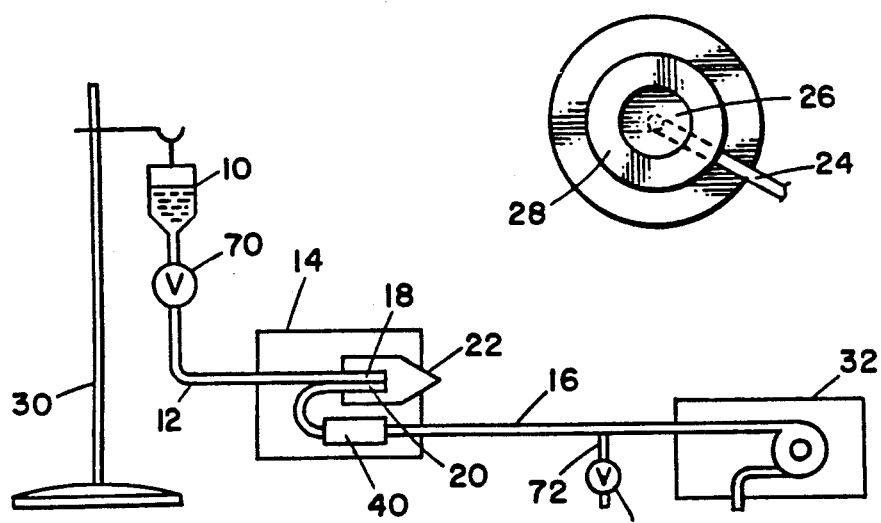
Fig. 2
Fig. 1
Fig. 3
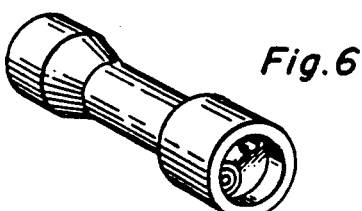
Fig. 6
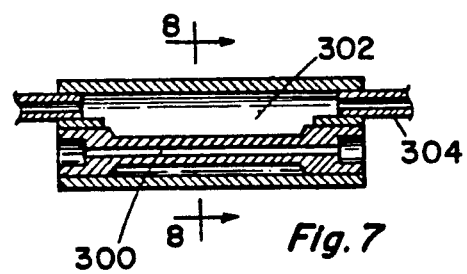
Fig. 7
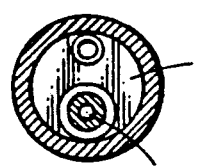
Fig. 8
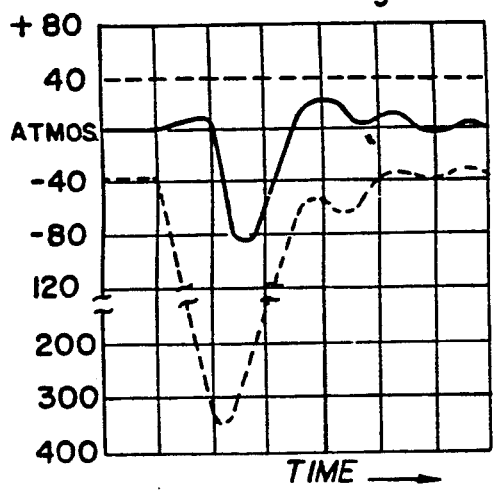
Fig. 4
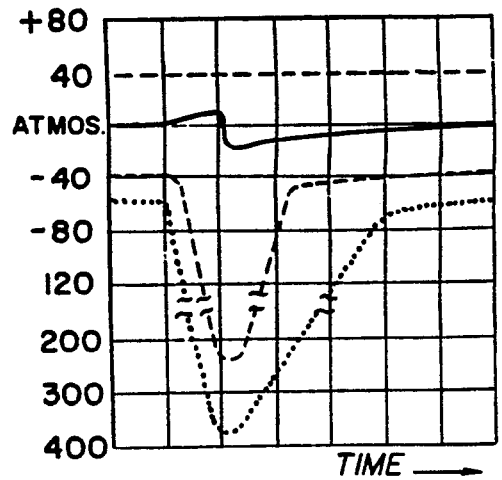
Fig. 5

EYE SURGERY APPARATUS WITH VACUUM SURGE SUPPRESSOR

This invention relates to methods and means for accomplishing surgical removal of material from the eye with increased safety.

BACKGROUND

A variety of procedures are currently being employed to accomplish removal of cataracts and other material from within the eye. One of those procedures is often referred to as an irrigation-aspiration method. It involves breaking, tearing or otherwise dividing the material to be removed into small fragments and aspirating those fragments from the eye into a fluid flow line by which they are carried away. Fluid pressure levels in the apparatus by which that procedure is practiced are dictated by the need to preserve pressure balance within the eye. More particularly, in the case of cataract removal, it is important to prevent or minimize collapse of the cornea into the cavity formed by removal of lens material. Difficulty in preventing such collapse has tended to discourage some surgeons from the use of the irrigation-aspiration method notwithstanding that it's successful use can result in substantially less discomfort to patients in the post operative period.

In the method, an incision is made on or about the corneal margin to gain access to the lens. A tool in the form of a probe which houses the outlet end of a fluid supply line and the inlet end of an aspiration line is inserted into the opening under the cornea. Some means is provided for dividing the lens material into small fragments. The means for dividing eye material may comprise no more than a cutting edge at or near the flow tube openings. More commonly an ultrasonically driven tool is included to aid in division of the material to be removed. The task is to separate that material and divide it into small pieces, aspirate that material from the eye and to replace the material so removed with water, actually a balanced, salt in water solution. The opening in which the probe is inserted is small, 6 millimeters or less, and the opening tends to close so that a substantially closed cavity is formed as lens material is removed. The water is disposed under the cornea and serves to prevent corneal collapse into the cavity. It is the water in that cavity that is used to aspirate and carry away lens material. Accordingly the flow of water to the lens cavity must equal the flow of water being removed by aspiration augmented by enough water to account for increase in lens cavity size. That flow ratio must be maintained while maintaining enough water in the lens cavity to prevent the cornea's collapse. The inner surface of the cornea is covered by a layer of irreplaceable endothelium cells. Collapse of the cornea would bring those cells into destructive contact with the removal tool. In the case of a sonically activated removal tool, collapse of the cornea into contact with the tool could result in puncture of the cornea. To accomplish the pressure balance to prevent those catastrophes requires precise control of supply water pressure and aspiration pressure. In practice, positive supply pressure is achieved by elevating the supply water container. Aspiration pressure is negative whereby the pressure at the lens cavity is close to atmospheric pressure.

Two primary factors tend to upset the desired pressure level at the eye. Negative pressure in the aspiration circuit is developed by a pump in most practical systems. Peristatic pumps are usually used but whatever the pump form, small cyclic variations in negative pressure occur and tend to make the cornea oscillate over the cavity being formed by the lens. A greater and more troublesome pressure variation occurs when an occlusion or partial occlusion of the aspiration opening is overcome. Occlusion occurs when a piece of eye material too large to pass through the aspiration inlet is drawn to it. Pressure in the aspiration line is forced more negative by the aspiration pump until the blocking material is divided or drawn into the inlet and the occlusion is cleared. When that occurs, the negative aspiration pressure, now greater in absolute value than the supply pressure, evacuates the lens cavity and collapses the cornea. In practice the supply water includes entrained air and there may be bubbles in the supply. The mass of the water and the compliance of the air line, coupled with the reduced flow resistance as the occlusion is overcome, act as an under damped oscillatory system in which the cornea may be vibrated violently as a function of the size of the cavity.

SUMMARY OF THE INVENTION

It is an object of the invention to provide an improved method and an improved means by which to conduct eye surgery with greater safety;

Still another object is to provide such improvements in a way that is inexpensive, is applicable to all current brands of irrigation-aspiration systems apparatus and requires less, not more, skill in performing such procedures as cataract removal.

These and other objects and advantages of the invention are realized in part by the provision of a method and apparatus which convert what is a normally underdamped irrigation-aspiration system to an overdamped system when an occlusion is cleared. It can be described as the method of minimizing corneal collapse during material removal from an eye by the irrigation-aspiration procedure using irrigation-aspiration apparatus which method comprises the steps of:

sensing an increase in negative pressure in the aspiration line of said apparatus; and increasing flow resistance in said aspiration line as an incident to having sensed said increase.

Stated another way, the objects and advantages of the invention stem, in part, from the provision of an article of manufacture for inclusion in the aspiration line of an irrigation-aspiration apparatus for conducting eye surgery by the irrigation-aspiration method the article comprising a flow tube the walls of which have sufficient renitence to maintain the flow path open at negative internal pressure values corresponding to the positive internal pressure values of the irrigation line of said apparatus, said walls being responsive to more negative internal pressures to deform to reduce the cross-sectional area of said flow path.

A tool is provided in the preferred form which comprises dividing means for dividing material found in the interior of an eye and two flow paths each having openings proximate to one another and to said dividing means. The tool further comprises a variable flow resisting element responsive to increasing negative pressure to increase it's resistance to flow connected in series with one of said flow paths.

THE DRAWINGS

In the drawings:

FIG. 1 is a schematic diagram of a presently preferred irrigation-aspiration apparatus for use in conducting cataract removal by the irrigation-aspiration method;

FIG. 2 is a schematic diagram of a fragment of the tool of the apparatus of FIG. 1 shown as it might appear while in use during cataract removal;

FIG. 3 is a simplified, cross-sectional view of the preferred vacuum controlled flow resistor.

FIG. 4 is a graph depicting pressure variations in the eye and in the supply and aspirating flow paths in a representative situation in the absence of the invention; and FIG. 5 is a graph depicting pressure variations in the eye and tool in a representative situation during use of the apparatus of FIG. 1 with the improvement of the invention in place;

FIG. 6 is a perspective view of a preferred form of double flowpath vacuum controlled flow resistor;

FIG. 7 is a cross-sectional view of another form of vacuum controlled resistor; and FIG. 8 is a cross-sectional view taken on line 8—8 of FIG. 7.

DESCRIPTION OF THE PREFERRED EMBODIMENT

The apparatus of FIG. 1 includes a source of irrigation fluid, a balanced salt in water solution, referred to here as water. It includes a tool for removing material from the inner eye, a supply line arranged to conduct water under positive pressure from the source to the tool, a means for developing a negative pressure and an aspiration line arranged to utilize the negative pressure to conduct water and removed material from the tool. The elements thus far described form an irrigation-aspiration system of conventional form. In this embodiment the source is the water container 10. The supply line is numbered 12. The tool is numbered 14 and the aspiration line is numbered 16. The supply line ends at 18 and the aspiration line begins at 20 in the tool 14.

The tool is mounted on a handle which is not shown here both because the handle per se does not form part of the invention and for the sake of clarity. The tool performs several functions. It must divide and sever the lens or other material to be removed. To that end it is formed with cutting edges at it's forward extremity at 22. Some tools incorporate ultrasonically activated elements to facilitate material division. The lens or other material is to be removed by aspiration into and along the aspiration line. The vehicle for aspiration is water which is supplied from the source 10 by line 12. The water is supplied at positive pressure by elevating the water container 10. In this case it is mounted on a pole 30. In a typical case it is mounted about 30 inches above the working level of the tool. The operating surgeon may control the supply pressure by having the bottle elevated or lowered in some degree. Negative pressure for aspiration is developed by any convenient means and in the case of most systems is developed by connecting the aspiration line to a pump. Peristaltic pumps are commonly used and it is such a pump that is depicted at 32 in FIG. 1.

The cross-sectional area of each of the supply and aspiration line ends is necessarily small because those ends must be placed in close proximity to the cutting edges and they and the cutting edges are inserted through an edge opening in the cornea into the lens to be viewed with a microscope during the removal phase of the procedure. That is depicted schematically in FIG. 2 wherein the end of the tool is numbered 24. It extends under the cornea 26 into the lens 28.

The conventional irrigation-aspiration apparatus includes a normally open, solenoid actuated clamp valve which may be mounted on the pump unit. The supply line is placed in the clamp structure such that it is pinched closed when the solenoid is closed by operation of a foot switch. Another valve, responsive to operation of the foot switch and located in an air inlet line, opens the aspiration line to atmosphere. They are also the only protection in the conventional system against the consequences of a step function increase in negative pressure in the cavity from which material is being removed. The primary occasion for such an increase is the sudden relief of a blockage of the aspiration tube inlet. If a corneal collapse is observed, the surgeon can pinch off the water supply, open the aspiration line to relieve the negative pressure, and stop the pump. However, those expedients do not solve the problem for at least two reasons. In practice the only means available to the surgeon for clearing a blockage are mechanical manipulation of the tool and the suction force at the aspiration line end. To use the suction force requires closing the air inlet line and operating the pump. Pressure in the eye cavity will drop immediately when the occlusion is cleared and pinching off the line and stopping the pump will ordinarily not prevent either the drop or the resulting collapse of the cornea. The other reason is that the only means the surgeon has to known that negative pressure must be reduced is to observe a corneal collapse which is akin to closing the barn door after the horse is gone. The supply line valve is numbered 70. The air inlet passage to the aspiration line is numbered 72 and it's air inlet valve is numbered 74.

The pressure variations attending an occlusion in the conventional system and the occlusion's relief are described graphically in FIG. 4 where y distance represents the magnitude of pressure and the x distance represents, in turn, a period prior to an occlusion of the aspiration line input, the time of an occlusion, a period over which it persists followed by the time of sudden relief of the occlusion and, finally, a period following relief. The supply and aspiration line ends have small flow path areas which present relative high resistance to flow. That factor serves to limit the rate of pressure change in the cavity formed by removal of lens material. Typical supply and aspiration lines have an inside diameter up to about 2 millimeters. However, the usual pump is capable of developing negative pressure up to about 500 millimeters of mercury to insure that the removed material will be aspirated through the small aspiration inlet. The upper dashed line in FIGS. 4 and 5 represents the pressure at which water arrives for discharge into the cavity. It's magnitude is determined by the height of the supply container. Accordingly it's magnitude is substantially constant. The lower dashed line of the graphs represents the negative pressure at the aspirating line inlet downstream from the occlusion and, in the case of FIG. 5, upstream from the vacuum controlled resistor. The dotted line in FIG. 5 represents pressure in the aspiration line downstream from the vacuum controlled resistor. If adjusted properly, the negative pressure at the aspiration line inlet balances the positive supply pressure so that cavity pressure, the solid line, corresponds to ambient atmospheric pressure in the absence of an occlusion. When occlusion occurs, flow resistance at the aspiration inlet approaches infinity. The pump pulls down the pressure in the aspiration line to a value substantially below normal operating value. The cavity pressure increases somewhat but the increase is limited because water leaks from the cavity via the incision.

When the occlusion is cleared, the sum of the positive supply pressure and the aspirating line pressure swings sharply negative and water is sucked from the cavity. The net negative pressure is overcome by initial inrush of water into the cavity line input so the cavity pressure rises rapidly to become less negative. The effect is to produce a decremental oscillation of cavity pressure. Oscillation magnitude, frequency and decay rate depend upon the mass and compliance of the water and the system elements and thus, in part, on cavity volume. The pressure excursions in the cavity effect collapse and flutter of the cornea.

That collapse and oscillation is largely overcome in the invention by the inclusion of a vacuum responsive, variable flow resistance element in the aspiration line. Such an element, a vacuum controlled resistor, is included in FIG. 1 where it is identified by the numeral 40. It forms part of the tool 14 in the preferred form. The effectiveness of the element is greatest when it is close to the aspiration line inlet.

Element 40 may have a variety of forms. Flow resistance in a flow line varies with cross-sectional area, flow path shape, obstruction configuration, length of restrictions and some other factors. It is currently preferred to employ a flow section in the aspiration line which will deform in response to increase in negative pressure to reduce the cross-sectional area of the flow path and which tends to reform to increase flow area when aspirating line pressure becomes less negative. The currently preferred element having that quality is depicted in FIG. 3 and is the element 40 of FIG. 1. It is shown in cross-section taken on a plane which contains its longitudinal axis. It is an elongated cylindrical tube having reduced outer wall diameter and it has reduced wall thickness, except at its ends. In relaxed condition the renitence of the tube forces it to substantially cylindrical shape. The cross-sectional area is approximately equal to the cross-sectional flow area, of the remainder of the aspiration line other than at the tool. In preferred form the section of reduced wall thickness is at least one quarter of an inch long and more preferably is about one inch long. The wall thickness in the reduced area is from 0.020 inches to 0.001 inches. It has a cross sectional flow area in relaxed condition between 0.0005 to 0.05 square inches and is formed of an inert elastomeric material, preferably a silicon rubber. It should collapse nearly completely at some negative pressure such that the pressure upstream from the vacuum controlled resistor does not exceed a value during an occlusion that will draw down the pressure in the eye cavity to about 50 millimeters of mercury below atmospheric pressure after the occlusion is cleared. The cornea may collapse if the negative pressure exceeds the value. Selection of the response characteristics is based on balancing the need for sufficient negative pressure at the cavity to overcome occlusions against the advantage of limiting the negative pressure surge on clearance by increasing aspiration line flow resistance. It is possible to find a workable design by conventional computation methods but only a minimum of experimentation is needed to find an entirely suitable wall thickness and reduced section length for any commercially available elastomeric tubing. If the vacuum controlled resistor is allowed to close the aspiration line completely, suction at the aspiration line inlet will not increase further. If the occlusion has not been cleared, suction is no longer available to clear it. The line must remain open in some degree to achieve clearance. As long as the line remains open in some degree, suction force is available by Pascal's Law to help clear the occlusion. The ideal element is one that collapses readily under negative pressure greater in absolute value than the positive supply pressure but which does not close the flow path completely unless the blockage is so severe that unduly high negative pressure would be developed upstream from the element. That complete closure feature need not be incorporated in the design of the element but it is included in the preferred embodiment as a gross safety measure. The pump controller can be arranged to cease pumping if negative pressure becomes excessive. Complete closure of the resistance element is then useful only in the event of failure of the pump controller to limit suction.

FIG. 5 illustrates that effect of the negative pressure responsive, variable resistance of the invention is to convert the system that is normally underdamped at the eye cavity to an overdamped system immediately on release of an occlusion. Again the pressure of the irrigation fluid, the supply water, is substantially constant before, during and after overcoming an occlusion with aspiration pressure. Following an occlusion, pressure in the cavity increases but the increase is slight because the water escapes at the incision from the space under the cornea. When an occlusion occurs, the pump "draws down" the aspiration line. The degree in which the pressure downstream from the cavity is permitted to go negative is determined by the negative pressure at which the variable resistance device, element 40, shuts off communication in the line. Comparison of FIG. 5 with FIG. 4 shows that the variable resistance device 40 has limited the negative pressure of the aspiration line upstream from the device to a lesser value in FIG. 5. When the occlusion is cleared in FIG. 5, the pressure of water in the eye cavity and the renitence of the variable resistance element tend to force the flow path of the variable resistance device to increased area and lower resistance. However, negative pressure downstream toward the pump tends to draw the device's walls to smaller area. Consequently, the device presents a considerably higher flow resistance at the beginning of the transition period which slowly decreases to a smaller value as the fluid flows through it. The net result is reduced rate of pressure change in the eye cavity and a much smaller and non-oscillatory negative pressure excursion and that translates into minimal corneal collapse.

The scale lines and the dashed cavity pressure lines in FIGS. 4 and 5 correspond substantially to oscilloscope scale lines and traces recorded during actual test of a system with the vacuum controlled resistor in the case of FIG. 5 and without it in the case of FIG. 4. The bottle was mounted 70 centimeters above the tool. The supply and aspiration lines had an inside diameter of 2 millimeters. The vacuum controlled resistor had a relaxed inside diameter of 0.06 inches. It had a wall thickness reduced to 0.005 inches over a length of one inch and was made of medium hardness, silicone rubber flow tube. It was located in series in the aspiration line eight inches from to aspiration line inlet. In FIGS. 4 and 5 the interval between adjacent vertical scale lines represents one volt or 40 millimeters of mercury. The interval between horizontal scale lines is 0.2 seconds. In both Figures the occlusion was cleared at 0.4 seconds. In FIG. 4 the eye cavity pressure dropped to about negative 90 millimeters of mercury. In FIG. 5, inclusion of the vacuum controlled resistor limited the drop in the eye cavity to less than 20 millimeters of Mercury. In FIG. 4, the undulations in the curve after 1 second result from pressure variation produced in the aspiration line by the peristaltic pump. Inclusion of the vacuum controlled resistor smoothes out those variations as shown by the solid line in FIG. 5.

In the experiment depicted in FIG. 5, the negative pressure in the aspiration line upstream from the vacuum controlled resistor reached about 250 millimeters of mercury. Increasing the wall thickness of the resistor to 0.006 inches resulted in an reduction of the peak pressure to negative 300 millimeters and an increase to a wall thickness to 0.007 inches resulted in a peak pressure reduction to about 350 millimeters of mercury. The ratio of change in peak negative pressure to wall thickness change can be reduced substantially, and the wall thickness dimension made less critical, by connecting two or more vacuum control resistors in parallel as shown in FIG. 6. In some cases the parallel arrangement may be preferred.

Another variation is shown in FIGS. 7 and 8. Here the exterior of the vacuum controlled resistor 300 is subjected to the pressure in a chamber 302 which is included in series in the water supply line 304. By this arrangement, the effect of the vacuum controlled resistor is made more uniform despite variation in the height of the supply water container. The degree in which flow resistance is increased is a joint function of the negative pressure in the aspiration line and the positive pressure in the supply line.

The particular embodiments described herein and which are shown in the drawings represent what are considered to be the best embodiments and modes of practicing the invention. However, it is to be understood that other embodiments and modes of practicing the invention are possible and the scope of the invention is not to be considered to be limited to what is shown and specifically described is to be limited instead by the scope of the appended claims. In this connection the term "vacuum controlled resistor" is intended to be a generic description rather than a designator of only the particular form shown and described.

We claim:

1. A system for performing surgery on an eye, wherein the surgery produces material, comprising:
    a supply line for providing a fluid to the eye;
    an aspiration line for removing said fluid and the material from the eye, said aspiration line having a first end near the eye and a second end opposite from said first end; and
    a flow tube having a fluid resistance and being connected to said aspiration line between said first and second ends of said aspiration line, said flow tube having a wall constructed to contract when the material from the human body causes the fluid pressure within said aspiration line to decrease to a predetermined value, wherein said flow tube fluid resistance increases such that said first end of said aspiration line will have a greater fluid pressure than said second end of said aspiration line.

2. The system as recited in claim 1, wherein said flow tube collapses when the fluid pressure within the flow line decreases to a predetermined value.

3. The system as recited in claim 1, wherein said flow tube has a cross-sectional area between 0.0005 and 0.05 inches and a wall thickness over a length greater than 0.15 inches which is between 0.02 and 0.001 inches.

4. The system as recited in claim 1, wherein said flow tube is surrounded by a chamber in fluid communication with said supply line, such that said wall movement is dependent upon said aspiration line and said supply line fluid pressures.

5. An apparatus within a flow line having a first point and a second point, the flow line having a fluid that flows from the first point to the second point, comprising:
    a flow tube having a fluid resistance and being connected to the flow line between the first and second points of the flow line, said flow tube having a wall constructed to collapse when the fluid pressure within the flow line decreases to a predetermined value, such that said flow tube resistance increases, said flow tube further having a cross-sectional area between 0.0005 and 0.05 inches and a wall thickness over a length greater than 0.15 inches which is between 0.02 and 0.001 inches.

6. An apparatus within an aspiration line of a system used to remove material from a human body, the aspiration line having a fluid that flows from a first point in the aspiration line to a second point in the aspiration line, comprising:
    a flow tube having a fluid resistance and being connected to the aspiration line between the first and second points of the aspiration line, said flow tube having a wall constructed to contract when the fluid pressure within the aspiration line decreases, such that said flow tube fluid resistance increases, said flow tube further having a cross-sectional area between 0.0005 and 0.05 inches and a wall thickness over a length greater than 0.15 inches which is between 0.02 and 0.001 inches.

* * * * *